United States Patent [19]

Mars

[11] Patent Number: 5,003,968
[45] Date of Patent: Apr. 2, 1991

[54] HEAD SUPPORT

[76] Inventor: Suzanne P. Mars, 23649 Duffield Rd., Shaker Hts., Ohio 44122

[21] Appl. No.: 509,466

[22] Filed: Apr. 16, 1990

[51] Int. Cl.⁵ .............................................. A61F 5/01
[52] U.S. Cl. .............................. 128/87 B; 128/76 R; 128/DIG. 19; 128/DIG. 23
[58] Field of Search .................... 128/84 R, 75, 76 R, 128/87 B, 89 A, DIG. 19, DIG. 23, 163, 164

[56] References Cited

U.S. PATENT DOCUMENTS

| | | | |
|---|---|---|---|
| 1,301,276 | 4/1919 | Kroetz | 128/87 B |
| 1,803,556 | 5/1931 | Nugent | 128/87 B |
| 2,796,866 | 6/1957 | Cohen | 128/DIG. 23 X |
| 2,807,260 | 9/1957 | Teufel | 128/87 B |
| 2,851,031 | 9/1958 | Ciampa | 128/75 |
| 2,904,040 | 9/1959 | Hale | 128/DIG. 23 X |
| 3,724,452 | 4/1973 | Nitsche | 128/75 |
| 4,854,306 | 8/1989 | Pujals, Jr. | 128/DIG. 23 X |

FOREIGN PATENT DOCUMENTS 577276  3/1932  Fed. Rep. of Germany ...... 128/164

OTHER PUBLICATIONS

Truax Greene Advertisement, 1893.
Orthopedic Appliance Atlas, p. 227, 1952.
Journal of Bone & Joint Surgery, 10/1983, p. 38.

*Primary Examiner*—Robert A. Hafer
*Assistant Examiner*—Kevin G. Rooney
*Attorney, Agent, or Firm*—Weston Hurd Fallon Paisley & Howley

[57] ABSTRACT

A head support for the physically disabied, particularly those suffering from cerebral palsy, is provided. The head support is comprised of a helmet, elastic tethers, a collar, a breastbone bridge, a waistband and two vertical straps. Optionally, a chin support may also be used. The elasticity and length of the tethers permit its head movement; but the system will return the head to its upright position. The head is held upright by the elastic tethers, from above. This flexible head support system is an improvement over existing rigid braces which are uncomfortable and often serve to increase spasticity of head and neck muscles. In addition, the present head support is aesthetically more pleasing than conventional rigid braces.

12 Claims, 3 Drawing Sheets

HEAD SUPPORT

BACKGROUND OF THE INVENTION

1. Field of the Invention

The invention relates to a device which enables people with reduced neuromuscular control of their head, to maintain their head in an upright position.

2. Description of the Prior Art

A number of people suffer from reduced neuromuscular control of their head, due to injury, disease, etc. One of the effects of reduced neuromuscular control is a drooping forward of the head; often times the condition being so severe that the chin rests on the front upper portion of the individual. This disability makes eating more difficult, and reduces social interactions, decreases the ability of the individual to observe their environment, impairs their airway, and can lead to skeletal deformities. These factors, along with the dropped head itself, have a negative social and psychological impact on the individual.

In an effort to correct this head drooping, a variety of braces have been devised which lift the head by preventing the downward movement of the chin. While many of these braces are successful in maintaining the head upright, their design has several drawbacks. These braces are typically very rigid; they maintain the patient in an extremely rigid upright posture. Maintaining an individual in such a rigid posture tends to increase spasticity, particularly in individuals already suffering from some form of spasticity, such as with cerebral palsy. The rigidity of these braces frequently eliminates voluntary head and neck movement, and causes discomfort at the point of contact between the person and the brace. Rigid devices which rely on holding the head up by forcing the chin upward also, make it more difficult for the individual to speak. In addition most of the braces available are aesthetically unpleasing, due to bulk, lack of streamlining and sense of mechanical devices.

Desirably, a head support would be available that would avoid the drawbacks of the rigid braces and yet hold the person's head in an upright position.

SUMMARY OF THE INVENTION

The present invention overcomes the foregoing drawbacks of the prior art and provides a new and improved head support comprising a helmet attached to the head, elastic tethers which connect the helmet to a collar, a waistband which affixes the device to the body and which serves to anchor the device; a strap which attaches the waistband to the back of the collar, a strap which attaches the waistband to the front of the collar, and a breastbone bridge which serves as a point of attachment for the left front and right front of the collar, the front strap running vertically from the waistband and the optional chin support.

The resulting head support maintains the head upright by supporting the head from above. Due to the presence of the elastic tethers which connect the helmet and the collar, greatly needed flexibility is provided; if desired, the optional chin support may be used to support the head and to maintain the head in a forward direction.

DESCRIPTION OF THE PREFERRED EMBODIMENT

Figure 2:
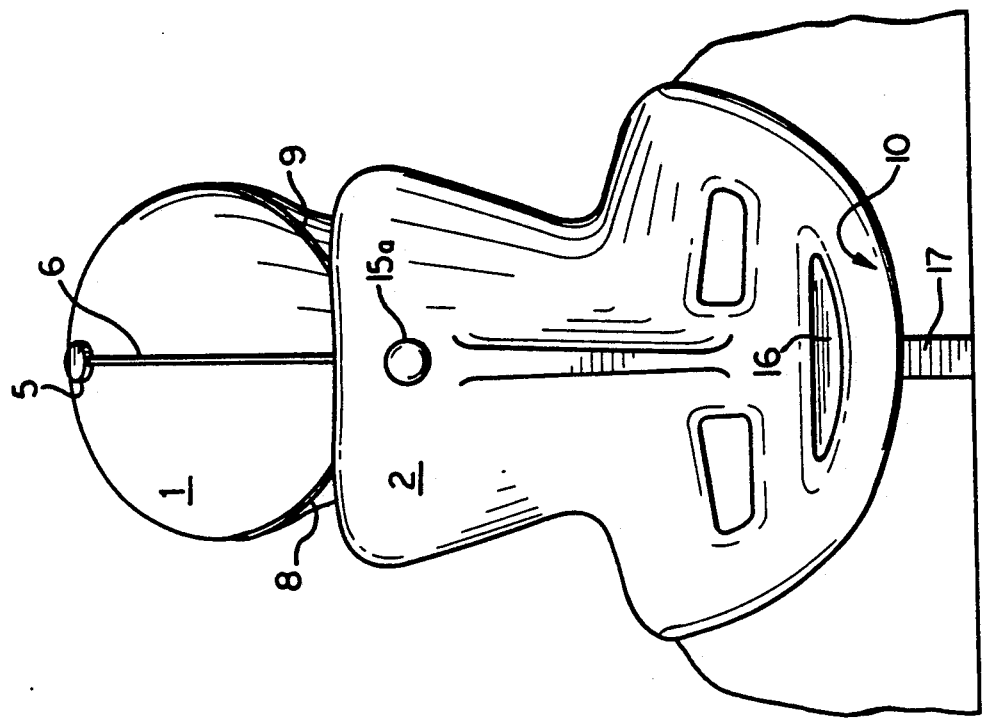
FIG. 2 is a rear elevational view when fitted on a person.
Figure 1:
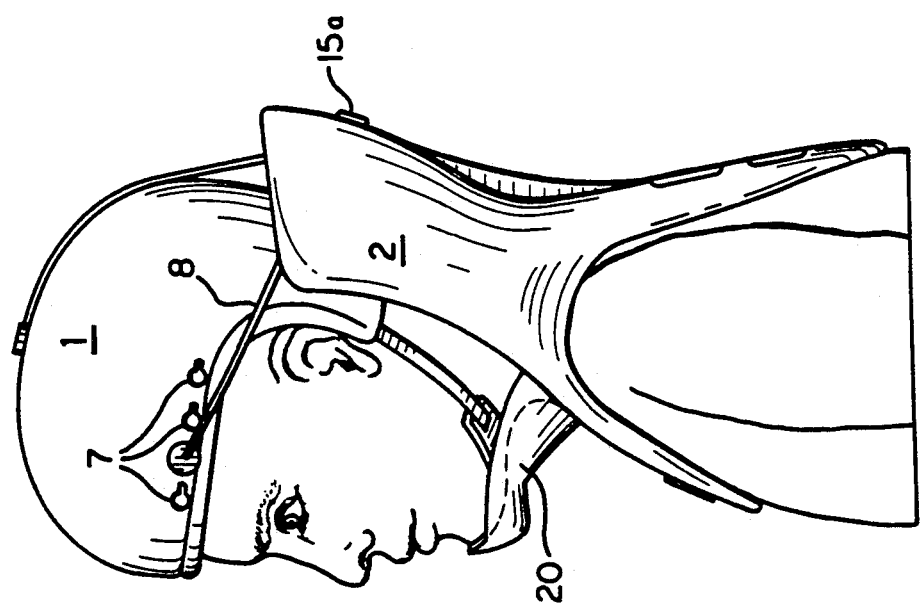
FIG. 1 is a side elevational view of the head support when fitted on a person.
Figure 5:
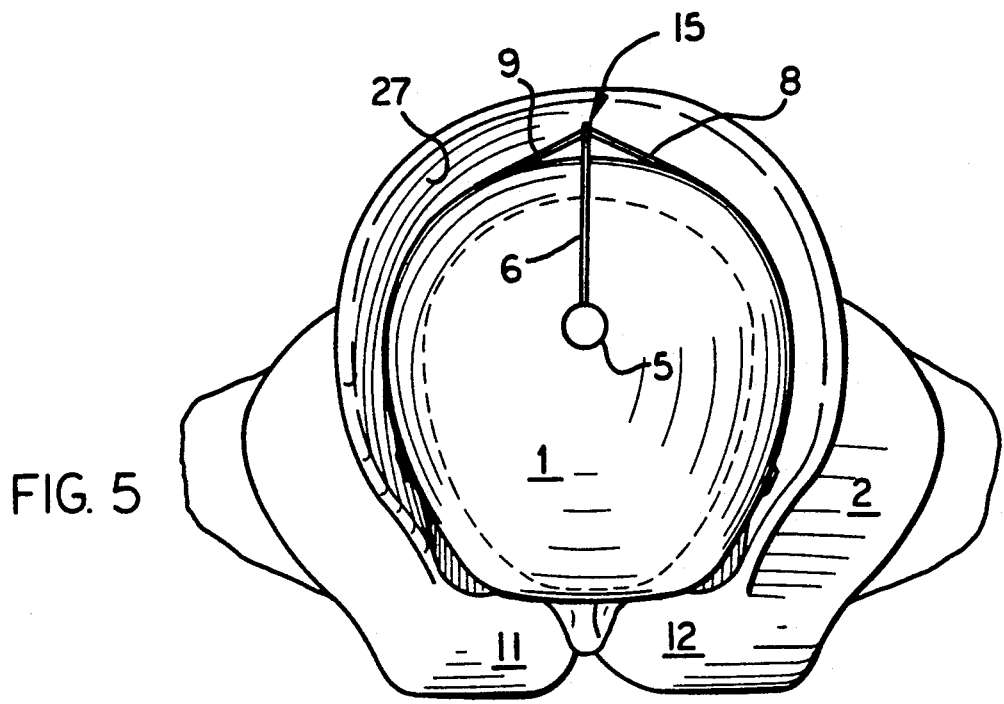
FIG. 5 is an overhead view when fitted on a person.
Figure 3:
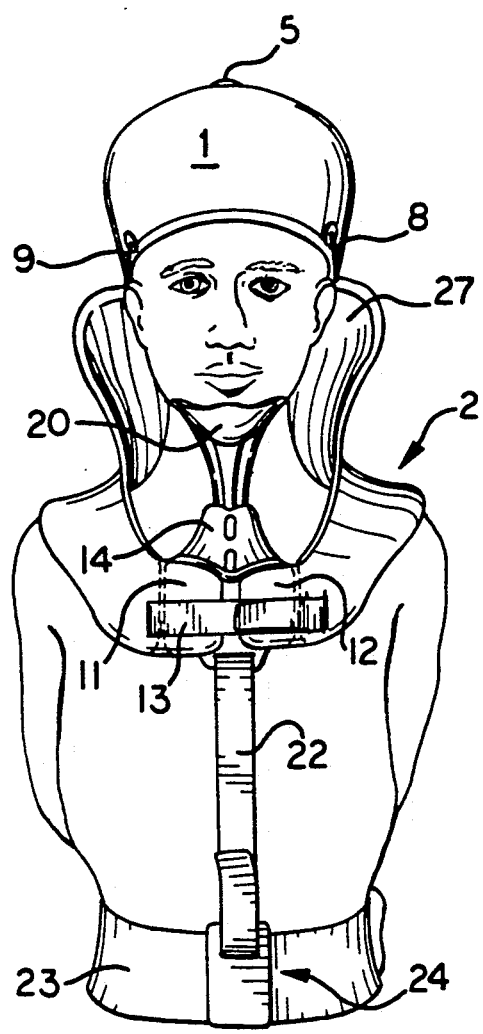
FIG. 3 is a front elevational view when fitted on a person.
Figure 4:
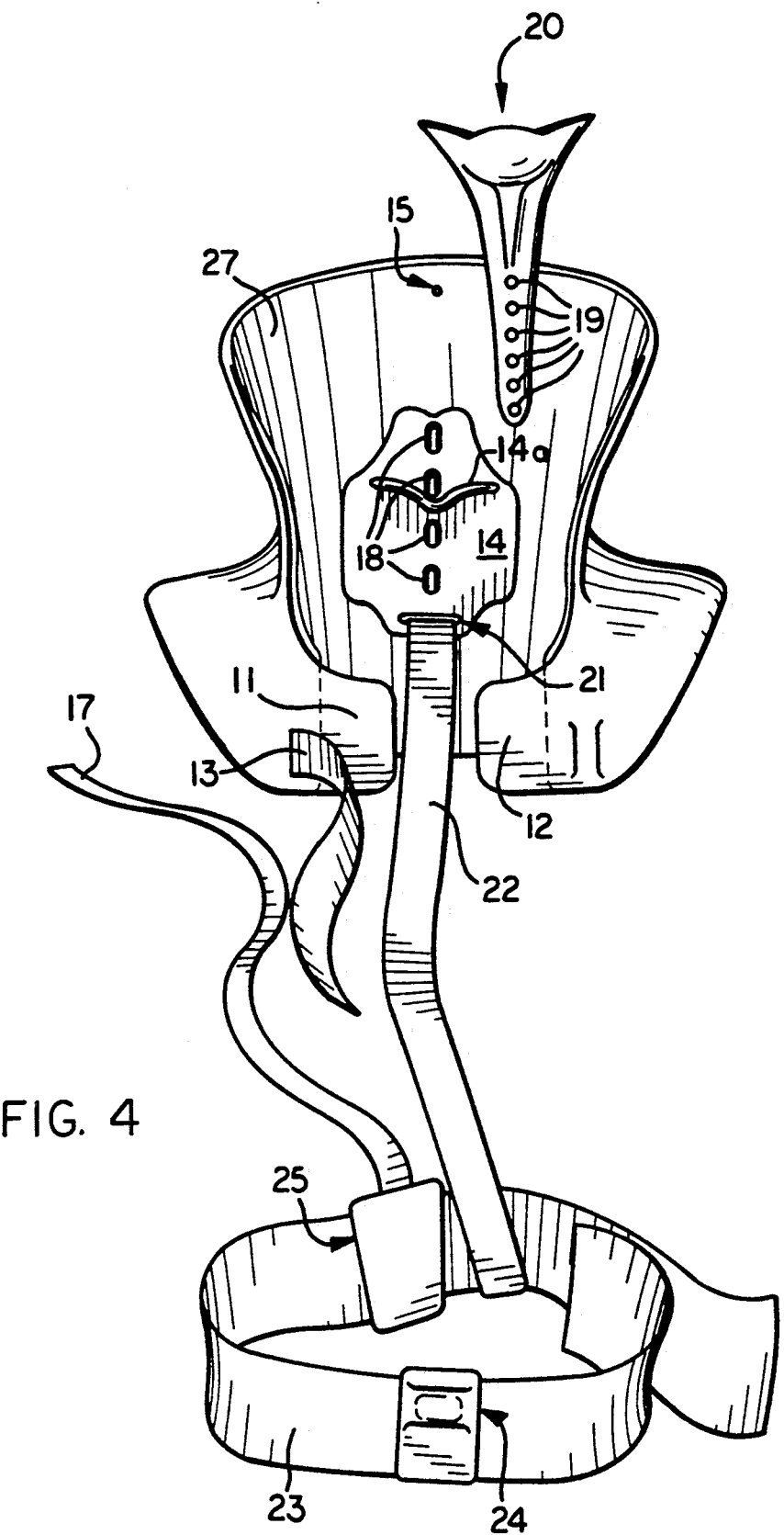
FIG. 4 is a front elevational view, not fitted on a person.

The present invention supports the head and keeps it upright, creates easier eating, provides an unobstructed airway, prevents skeletal deformities, increases an individual's ability to receive visual stimulation, improves the social/psychological functioning of an individual, reduces discomfort, and reduces spasticity of the head, neck and upper body muscles.

The head support is aesthetically pleasing, generally shaped to the contours of the human body and symmetrical. The head support provides a responsive system which permits movement of the head yet still holding the head upright.

THE HELMET

The helmet 1, the portion of the device which attaches directly to the head, may be made of a great variany of materials known in the art, preferably lightweight materials such as aluminum, injection-molded plastic, or strong textiles. The helmet may be a solid piece, or it may be comprised of individual straps or a mesh. In the preferred embodiment, a solid helmet was chosen for aesthetic reasons. The helmet has a means for attaching the helmet directly to the person's head, preferably a strap 4 which runs from one side of the helmet under the person's chin to the other side of the helmet. The fit of the chin strap may be adjusted by a means known to one skilled in the art of such as a buckle or preferably a hook and eye fastener available under the tradename VELCRO. At the crown of the helmet there is a means 5 for attaching an elastic tether 6. Similarly, on either side of the helmet near the edge and preferably midway between the front and back of the helmet, there are multiple means 7 for attaching elastic tethers 8,9. The multiple attachment points make it easy to adjust lateral support of the head not only for comfort but also to correct for a drooping of the head to one side or the other.

THE COLLAR

The collar 2 may be made of a single component, such as by injection molding, or multiple pieces fitted together to provide a rigid structure. The collar rests on the shoulders of the individual. It extends down over the back of the individual below the shoulder blades. The bottom edge is shown as 10. The collar extends upward along the back of the neck to approximately a height that would be between mid and top of the ear of the individual. This upper portion of the back of the collar extends forward to a point behind the ear. The upper back portion of this collar is shaped to approximate the contours of the human neck. While the collar rests on the shoulders, it does not project outward beyond the shoulders. Limiting the projection over the shoulders not only serves to reduce bulk, but prevents a restriction of shoulder and arm movement. Furthermore, shoulder and arm movement are less likely to cause the collar to shift since the collar does not project over the shoulder. The collar extends down along each side of the wearer over the front of the individual across the clavicle and which terminates at the centerline of the individual approximately over the breastbone. For ease in putting the collar on, the collar is split vertically along the line of the breastbone. The front ends 11,12 of the collar may be brought together, for a more secure fit, by means of a strap 13 fixed to one side of the front of the collar, which may be adjustably affixed on the other side of the collar. These front ends of the collar fit over the breastbone bride 14, held in place by ridge 17 on the breastbone bridge 14.

At the midline of the back of the collar on interior surface 27 of the collar, approximately from about ¼ to about 2 inches, preferably 1 inch from the top back edge of the collar there is a means 15 for attaching the elastic tethers to the collar. Also centered along the back midline of the collar is a slot 16 several inches from the bottom back edge of the collar, through which the back strap 17 from the waistband is threaded.

ELASTIC TETHERS

There are a plurality of elastic tethers, 6, 8, 9 preferably three. Each tether has a first end and a second end; the first end attaches to the helmet. The second of each tether attaches to the same point on the collar. This may be accomplished by joining the ends of the tethers so that there is a single attachment point to the collar. While the tethers may be any suitable elastic material capable of supporting the weight of a person's head, good results have been obtained using an elastic tether marketed under the tradename BUNJI chord.

A first tether attaches to the crown of the helmt; a second tether attaches to the right side of the helmet; and a third tether attaches to the left side of the helmet. The first tether measures from about 8 inches to about 18 inches in length. The second tether measures from about 8 inches to about 18 inches in length. The third tether measures from about 8 inches to about 18 inches in length. The length of the tether depends on the elasticity of the tethers. Although the means for attaching the first ends of the tethers to the helmet and the second ends of the tethers to the collar may be accomplished by a means known to one skilled in the art, results have been obtained using a keyhole shaped hole in the helmet and the collar; a peg type device is placed on both the first and second ends of the tethers. These pegs are frictionally pitted into the keyholes.

The length of the elastic tether may vary depending on the elasticity of the elastic tether. The elastic tethers permit movement not only due to their elasticity but also due to their length.

BREASTBONE BRIDGE

The front surface of the breastbone bridge 14 has a ridge 17 which serves to accommodate and hold in place the top edge front ends 11,12 of the collar. In addition, the front bridge piece contains a plurality of vertically arranged holes 18 which accept corresponding projections 19 on the optional chin support 20. The bottom edge of the breastbone bridge contains a horizontal slot 21 through which the front vertical strap 22 is threaded.

WAISTBAND

The waistband 23 is a flexible strap made of a lightweight, durable material such as nylon webbing. The length of the waistband may be adjusted to fit snugly around the waist of the wearer. The attachment for the two ends of the waistband may be through fasteners known to those skilled as the art such a buckle or preferably the hook and eye fasteners available under the tradename VELCRO. The length of the belt is such that it may accommodate the waist of different size individuals. The belt width may vary; however, for comfort of the wearer it should be between three to six inches, most preferably about three inches. At the front center of the Waistband there are means 24 for attachment for a vertical strap 22 and at the back center of the waistband there are means for attachment of vertical strap 17. Preferably means 24,25 of attachment contains a horizontal slot through which the vertical strap may be threaded. The waistband serves not only as a means of attachment of the device to the back, but also anchors the device. In addition, the waistband counteracts the forward thrust of the droop or forward lean, of the head.

VERTICAL STRAPS

The invention contains two flexible vertical straps 17,22 made of a flexible material such as nylon webbing. The width of the straps are not critical; they can be from about one-half inch wide (depending on the strength of the material) to approximately five inches wide; preferably one inch wide. One end of vertical strap 17 contains a means for attachment to the waistband, the other end contains a means for attachment to a horizontal slot 16 on the collar. Similarly, one end of strap 22 contains a means for attachment to the waistband, the other end contains a means for attachment to the horizontal slot 21 in the breastbone bridge. In the preferred embodiment the ends of these straps are threaded through a horizontal slot; the direction of the strap is then reversed and the end of the strap is affixed to itself, preferably by means such as VELCRO.

CHIN SUPPORT

The chin support 20 is an optional attachment. It is shaped to follow the contour of the chin and neck. At the point where the chin support comes in contact with the chin there is a depression 26 to accommodate the chin. The lower front surface of the chin support contains projections 19 which provide a means for attachment, by frictionally fitting into the holes 18 in breastbone bridge 14. The front surface of the chin support is attached to the rear surface of the breastbone bridge. The pegs in the chin support are arranged vertically; a number of pegs are provided so that the height of the chin support may be adjusted. The chin support serves to support the head from below, and to orient the head so that the person is facing directly forward. However, this additional support from below is not necessary is since the head is already being supported from the above by the elastic tethers.

While one embodiment of the invention has been shown and described, various adaptations and modifications could be made without departing from the scope of the invention as defined in the appended claims.

What is claimed is:

1. A device to flexibly hold a head upright from above, comprising:
   a collar adapted to fit over human shoulders;
   a helmet adapted to fit a human head and to be retained in place;
   an elastic support means having a first end and a second end, the first end connected to the helmet, and the second end connected to the collar;

a waistband for attaching the device to the body;
a first strap having a first end and a second end;
a second strap having a first end and a second end;
a breastbone bridge connected to the front of the collar and the first end of the first strap; and
wherein the first end of the second strap is connected to the collar, the second end of the second strap is connected to the back of the waistband, said second strap serving to anchor the back of the collar to the waistband and the second end of the first strap is connected to the front of the waistband, said first strap serving to anchor the breast bone bridge and connected collar to the waistband.

2. The device of claim 1, further including a chin support, which is connected to the breastbone bridge.

3. The device of claim 1, wherein the breastbone bridge comprises a plurality of holes for attachment of the chin support.

4. The device of claim 1, wherein the breastbone bridge includes a ridge for holding the upper edge of the collar front ends in place.

5. The device of claim 1, wherein the breastbone bridge contains a horizontal slot through which the first strap may be threaded.

6. The device of claim 1, wherein the collar includes a means for attaching the elastic support means to the collar.

7. The device of claim 1, wherein the collar is split along the midline over the breastbone and includes a strap means to adjust the fitting of the collar.

8. The device of claim 1, wherein the helmet comprises a means for attachment of the elastic support means.

9. The device of claim 1, wherein the elastic support means comprises a plurality of elastic tethers.

10. The device of claim 1, wherein the elastic support means comprises three elastic tethers.

11. The device of claim 1 wherein the length of elastic support means is from about 8 inches to about 18 inches.

12. The device of claim 1, wherein the helmet includes a means for securely attaching the helmet to the head.

* * * * *